United States Patent
Nash et al.

(10) Patent No.: US 11,331,456 B2
(45) Date of Patent: May 17, 2022

(54) MULTILAYER BALLOONS

(71) Applicant: Medtronic Vascular, Inc., Santa Rosa, CA (US)

(72) Inventors: Stephen Nash, Clonellan (IE); Aram Jamous, Athenry (IE); Colin Meade, Westmeath (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 283 days.

(21) Appl. No.: 16/790,259

(22) Filed: Feb. 13, 2020

(65) Prior Publication Data
US 2020/0180246 A1    Jun. 11, 2020

Related U.S. Application Data

(62) Division of application No. 15/592,251, filed on May 11, 2017, now Pat. No. 10,596,773.

(51) Int. Cl.
*A61M 25/10* (2013.01)
*B29C 48/09* (2019.01)
(Continued)

(52) U.S. Cl.
CPC ............. *A61M 25/10* (2013.01); *A61F 2/958* (2013.01); *A61M 25/1029* (2013.01);
(Continued)

(58) Field of Classification Search
CPC ...... A61M 25/10–2026/1097; A61M 25/1029; A61M 2025/1075; A61M 2025/1081;
(Continued)

(56) References Cited

U.S. PATENT DOCUMENTS 5,478,320 A * 12/1995 Trotta .................. A61M 25/10
                                                                     604/103.06
5,512,051 A    4/1996 Wang et al.
(Continued)

FOREIGN PATENT DOCUMENTS

EP    1962939 A1    9/2008
EP    2394690 A1    12/2011
(Continued)

OTHER PUBLICATIONS

Chinese Office action for Application No. 201880031091.1, dated Jun. 1, 2021, 15 pages, with English Translation.
(Continued)

*Primary Examiner* — Diane D Yabut
*Assistant Examiner* — Brigid K Byrd
(74) *Attorney, Agent, or Firm* — Stinson LLP

(57) ABSTRACT

An example medical device includes a balloon that is inflatable to an inflated configuration. The balloon includes a non-compliant layer coextruded on an inner layer, and an outer layer coextruded on the non-compliant layer. The non-compliant layer is configured to delaminate from the inner and the outer layers in the inflated configuration. The non-compliant layer may be configured to rupture in the inflated configuration. An example technique includes inflating the balloon to a predetermined pressure sufficient to rupture the non-compliant layer and insufficient to rupture both the inner and outer layers. The example technique further includes deflating the balloon, and introducing the balloon into a vasculature. Another example technique includes coextruding a non-compliant layer on an inner layer, coextruding an outer layer on the non-compliant layer, and forming a balloon from the inner layer, the non-compliant layer, and the outer layer.

20 Claims, 4 Drawing Sheets

(51) Int. Cl.
  *B29C 48/21* (2019.01)
  *B29C 48/23* (2019.01)
  *B29C 48/151* (2019.01)
  *A61F 2/958* (2013.01)
  *B29C 71/02* (2006.01)
  *B29K 23/00* (2006.01)
  *B29K 79/00* (2006.01)
  *B29L 31/00* (2006.01)

(52) U.S. Cl.
  CPC ............ *B29C 48/09* (2019.02); *B29C 48/151* (2019.02); *B29C 48/21* (2019.02); *B29C 48/23* (2019.02); *A61M 2025/1075* (2013.01); *B29C 71/02* (2013.01); *B29C 2071/022* (2013.01); *B29K 2023/065* (2013.01); *B29K 2079/085* (2013.01); *B29L 2031/7543* (2013.01)

(58) Field of Classification Search
  CPC ...... A61M 29/02; A61M 25/1011–2025/1015; A61M 25/2509; A61M 25/2072; A61M 25/105; A61F 2/958; A61F 2/95–97; B29L 2031/7543
  See application file for complete search history.

(56) References Cited

U.S. PATENT DOCUMENTS

| | | |
|---|---|---|
| 5,908,406 A | 6/1999 | Ostapchenko et al. |
| 7,828,766 B2 | 11/2010 | Durcan |
| 8,052,638 B2 | 11/2011 | Lee et al. |
| 8,394,055 B2 | 3/2013 | Durcan |
| 8,535,596 B2 | 9/2013 | Durcan |
| 8,703,260 B2 | 4/2014 | Simpson et al. |
| 8,771,332 B2 | 7/2014 | Johnson et al. |
| 9,352,135 B2 | 5/2016 | Simpson et al. |
| 9,579,492 B2 | 2/2017 | Simpson et al. |
| 9,707,381 B2 | 7/2017 | Durcan |
| 10,596,773 B2 | 3/2020 | Nash et al. |
| 2003/0149468 A1 | 8/2003 | Wallsten |
| 2006/0008606 A1 | 1/2006 | Horn et al. |
| 2007/0167973 A1 | 7/2007 | Stupecky et al. |
| 2010/0234875 A1 | 9/2010 | Allex et al. |
| 2014/0276400 A1 | 9/2014 | Le |
| 2015/0105815 A1 | 4/2015 | Horn et al. |
| 2015/0290434 A1 | 10/2015 | Lin et al. |
| 2018/0161040 A1* | 6/2018 | Martin ................ A61M 25/104 |

FOREIGN PATENT DOCUMENTS

| | | |
|---|---|---|
| EP | 2397183 A1 | 12/2011 |
| JP | 4972651 A | 7/2012 |
| WO | 200164278 A1 | 9/2001 |
| WO | 2013040522 A2 | 3/2013 |

OTHER PUBLICATIONS

Extended European Search Report for Application No. 21168130.9, dated Aug. 31, 2021, 9 pages, Berlin.
International Search Report and Written Opinion of International Application No. PCT/US2018/031827, dated Jul. 6, 2018, 14 pp.
International Preliminary Report on Patentability from International Application No. PCT/US2018/031827, dated Nov. 21, 2019, 8 pp.
Prosecution History for U.S. Appl. No. 15/592,251, dated Nov. 16, 2018 through Feb. 19, 2020, 117 pp.

* cited by examiner

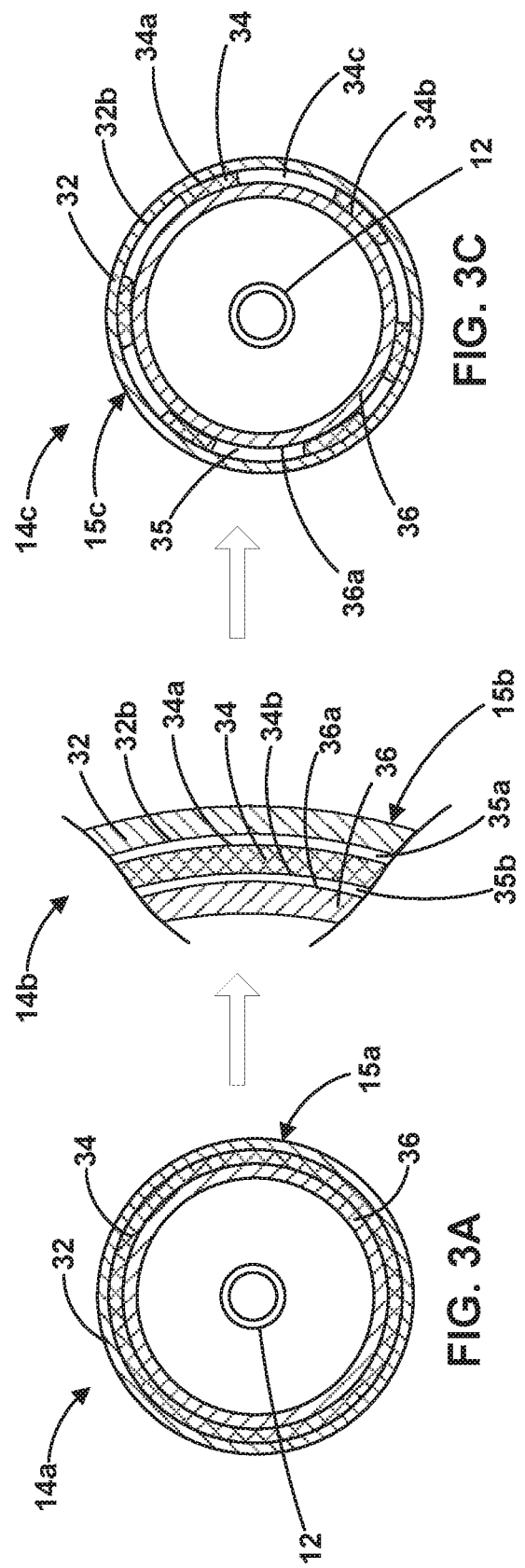
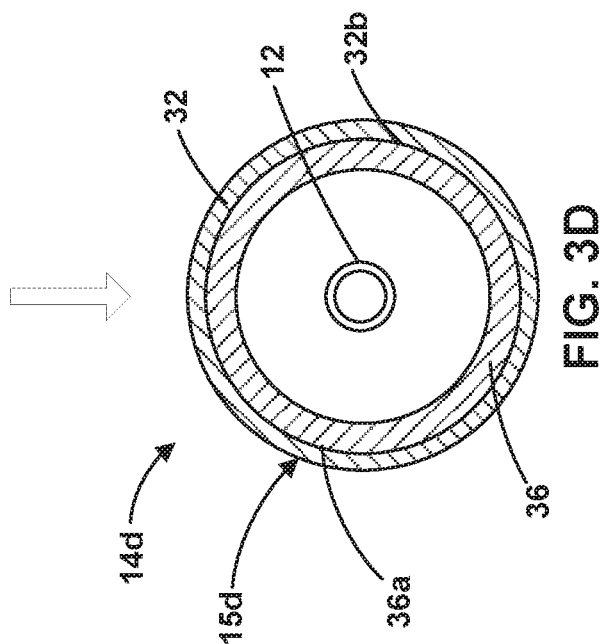

MULTILAYER BALLOONS

This application is a divisional of U.S. patent application Ser. No. 15/592,251, entitled, "MULTILAYER BALLOONS," and filed on May 11, 2017, the entire content of which is hereby incorporated by reference.

TECHNICAL FIELD

This disclosure relates to medical devices including balloons.

BACKGROUND

Catheters may be used in intravascular procedures or other procedures to facilitate minimally invasive access to a target site. For example, an angioplasty catheter may include balloons mounted to the catheter that may be advanced to the target site and inflated to clear or compress a blockage, for example a stenosis. As another example, a stent delivery catheter may include a stent positioned over a balloon, which may be inflated to deploy the stent.

SUMMARY

Example medical devices include multilayer balloons are described herein. In some examples, a multilayer balloon includes nested balloons, and may have a higher burst pressure than a single layer or single wall balloon having a wall thickness equivalent to the combined wall thickness of the multilayer balloon. Arranging, nesting, and inflating balloons to form multilayer balloons with uniform inflation characteristics may be relatively difficult or inefficient. Some example techniques according to the disclosure allow manufacturing a multilayer balloon from a single extrusion.

Clause 1: In some examples, a medical device includes a balloon inflatable to an inflated configuration. The balloon includes a non-compliant layer coextruded on an inner layer, and an outer layer coextruded on the non-compliant layer. The non-compliant layer is configured to delaminate from the inner and the outer layers in the inflated configuration.

Clause 2: In some examples of the medical device of clause 1, the non-compliant layer is configured to delaminate from the inner layer before delaminating from the outer layer.

Clause 3: In some examples of the medical device of clause 1, the non-compliant layer is configured to delaminate from the outer layer before delaminating from the inner layer.

Clause 4: In some examples of the medical device of any of clauses 1 to 3, the inner layer and the outer layers are more flexible than the non-compliant layer.

Clause 5: In some examples of the medical device of any of clauses 1 to 4, the non-compliant layer is configured to rupture in the inflated configuration at a predetermined pressure, wherein the predetermined pressure is insufficient to rupture both the inner and the outer layers.

Clause 6: In some examples of the medical device of clause 5, the non-compliant layer is configured to rupture after delamination of the non-compliant layer from the inner and outer layers.

Clause 7: In some examples of the medical device of clause 5, the non-compliant layer is configured to fragment in the inflated configuration at the predetermined pressure.

Clause 8: In some examples of the medical device of clause 7, an inner surface defined by the outer layer is configured to contact an outer surface defined by the inner layer in the inflated configuration.

Clause 9: In some examples of the medical device of clause 8, the inner layer defines an inner balloon and the outer layer defines an outer balloon, the inner balloon being nested in the outer balloon.

Clause 10: In some examples of the medical device of clause 9, the inner balloon is fluidically isolated from the outer balloon.

Clause 11: In some examples of the medical device of any of clauses 1 to 10, the non-compliant layer has a greater stiffness than each of the inner layer and the outer layer.

Clause 12: In some examples of the medical device of any of clauses 1 to 11, the non-compliant layer includes a thermoplastic.

Clause 13: In some examples of the medical device of clause 12, the thermoplastic includes a high-density polyethylene (HDPE).

Clause 14: In some examples of the medical device of any of clauses 1 to 13, one or both of the inner layer and the outer layer includes a thermoplastic elastomer.

Clause 15: In some examples of the medical device of clause 14, the thermoplastic elastomer includes a polyether block amide (PEBA).

Clause 16: In some examples of the medical device of any of clauses 1 to 15, the non-compliant layer is coextensive with one or both of the inner layer and the outer layer.

Clause 17: In some examples of the medical device of any of clauses 1 to 16, the non-compliant layer defines at least one of a discontinuity, a perforation, a window, or an opening in the inflated configuration.

Clause 18: In some examples, a system includes the medical device of any of clauses 1 to 17 and a second medical device secured to the balloon.

Clause 19: In some examples of the system of clause 18, the second medical device includes a stent crimped to the balloon.

Clause 20: In some examples, a system includes the medical device of any of clauses 1 to 17, and further includes an elongated member. The balloon is mounted to the elongated member. The elongated member includes a catheter body.

Clause 21: In some examples, a medical device includes a balloon inflatable to an inflated configuration. The balloon includes a non-compliant layer coextruded on an inner layer, and an outer layer coextruded on the non-compliant layer. The non-compliant layer is configured to rupture in the inflated configuration at a predetermined pressure. The predetermined pressure is insufficient to rupture both the inner and the outer layers.

Clause 22: In some examples of the medical device of clause 21, the non-compliant layer is configured to delaminate from the inner and the outer layers before the rupture.

Clause 23: In some examples of the medical device of clause 21 or clause 22, the non-compliant layer has a greater stiffness than each of the inner layer and the outer layer.

Clause 24: In some examples of the medical device of any of clauses 21 to 23, the balloon is in the inflated configuration at the predetermined pressure, and the non-compliant layer is ruptured such that the non-compliant layer defines a plurality of perforations.

Clause 25: In some examples of the medical device of any of clauses 21 to 23, the balloon is in the inflated configuration at the predetermined pressure, and the non-compliant is substantially disintegrated such that an inner surface defined by the outer layer substantially uniformly contacts an outer surface defined by the inner layer.

Clause 26: In some examples of the medical device of any of clauses 21 to 23, the non-compliant layer defines at least one of a discontinuity, a perforation, a window, or an opening in the inflated configuration.

Clause 27: In some examples, a method includes inflating a balloon to a predetermined pressure. The balloon includes a non-compliant layer coextruded on an inner layer and an outer layer coextruded on the non-compliant layer. The predetermined pressure is sufficient to rupture the non-compliant layer and insufficient to rupture both the inner and the outer layers. The method includes deflating the balloon, and introducing the balloon into vasculature of a patient.

Clause 28: In some examples of the method of clause 27, inflating the balloon at the predetermined pressure includes causing only the non-compliant layer to rupture to cause an inner surface defined by the outer layer to contact an outer surface defined by the inner layer.

Clause 29: In some examples of the method of clause 27, inflating the balloon at the predetermined pressure includes causing only the non-compliant layer to rupture to cause the non-compliant layer to define at least one of a discontinuity, a perforation, a window, or an opening in the inflated configuration.

Clause 30: In some examples, the method of any of clauses 27 to 29 further includes, after introducing the balloon into the vasculature, pressurizing the balloon to an operational pressure.

Clause 31: In some examples, a method includes inflating a balloon to a predetermined pressure. The balloon includes a non-compliant layer coextruded on an inner layer and an outer layer coextruded on the non-compliant layer. The predetermined pressure is sufficient to delaminate the non-compliant layer from the inner and the outer layers. The method includes deflating the balloon, and introducing the balloon into vasculature of a patient.

Clause 32: In some examples, the method of clause 31 further includes, after introducing the balloon into the vasculature, pressurizing the balloon to an operational pressure.

Clause 33: In some examples, a method includes coextruding a non-compliant layer on an inner layer, coextruding an outer layer on the non-compliant layer, and forming a balloon from the inner layer, the non-compliant layer, and the outer layer. The non-compliant layer is configured to delaminate from the inner and the outer layers in an inflated configuration of the balloon.

Clause 34: In some examples of the method of clause 33, co-extruding the non-compliant layer on the inner layer and coextruding the outer layer on the non-compliant layer includes coextruding a tubing including the inner layer, the non-compliant layer, and the outer layer.

Clause 35: In some examples of the method of clause 33 or clause 34, the forming the balloon includes molding the inner layer, the non-compliant layer, and the outer layer over a scaffold.

Clause 36: In some examples, the method of any of clauses 33 to 35 further includes heat-setting the balloon.

Clause 37: In some examples, the method of any of clauses 33 to 36 further includes inflating the balloon to a predetermined pressure sufficient to rupture the non-compliant layer, the predetermined pressure is insufficient to rupture both the inner and the outer layers.

Clause 38: In some examples, the method of clause 37 further includes allowing only the non-compliant layer to fragment at the predetermined pressure to cause an inner surface defined by the outer layer to contact an outer surface defined by the inner layer.

Clause 39: In some examples, the method of any of clauses 33 to 38 further includes securing a second medical device to the balloon.

Clause 40: In some examples, the method of clause 39 includes securing the second medical device to the balloon includes crimping a stent to the balloon.

Clause 41: In some examples, the method of any of clauses 33 to 40 further includes mounting the balloon to an elongated member.

Clause 42: In some examples, a method includes coextruding a non-compliant layer on an inner layer, coextruding an outer layer on the non-compliant layer, and forming a balloon from the inner layer, the non-compliant layer, and the outer layer. Only the non-compliant layer is configured to rupture in an inflated configuration of the balloon at a predetermined pressure.

Clause 43: In some examples of the method of clause 42, co-extruding the non-compliant layer on the inner layer and coextruding the outer layer on the non-compliant layer includes coextruding a tubing including the inner layer, the non-compliant layer, and the outer layer.

Clause 44: In some examples of the method of clause 42 or clause 43, the forming the balloon includes molding the inner layer, the non-compliant layer, and the outer layer over a scaffold.

Clause 45: In some examples, the method of any of clauses 42 to 44 further includes heat-setting the balloon.

Clause 46: In some examples, the method of any of clauses 42 to 45 further includes inflating the balloon to the predetermined pressure to delaminate the non-compliant layer from the inner and the outer layers.

Clause 47: In some examples, the method of any of clauses 42 to 46 further includes securing a second medical device to the balloon.

Clause 48: In some examples of the method of clause 47, securing the second medical device to the balloon includes crimping a stent to the balloon.

Clause 49: In some examples, the method of any of clauses 42 to 48 further includes mounting the balloon to an elongated member.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 3A is a schematic and conceptual cross-sectional view of the balloon of FIG. 1 in a partly inflated configuration, where the cross-section is taken in a direction orthogonal to a longitudinal axis of the medical device.

FIG. 3B is a schematic and conceptual expanded view of the cross-sectional view of the balloon shown in FIG. 3A with the balloon in an inflated delaminated configuration.

FIG. 3C is a schematic and conceptual cross-sectional view of the balloon of FIG. 3A including a middle layer of the balloon in an inflated perforated configuration.

FIG. 3D is a schematic and conceptual cross-sectional view of the balloon of FIG. 3A with an inner layer of the balloon contacting an outer layer of the balloon.

DETAILED DESCRIPTION

In examples described herein, a multilayer balloon configured to expand from a deflated configuration to an inflated configuration includes at least three layers. An example multilayer balloon may be prepared by coextrusion, for example, a trilayer extrusion. The inner and outer layers of the multilayer balloon may include materials having the same composition or having different compositions. The middle layer may include a material that has poor adhesion properties to the inner and outer layers, thus causing delamination of the middle layer from the inner and outer layers and the separation of the inner and outer layers from each other. The delamination could be activated during the extrusion of the multilayer balloon, for example, when the extrusion is under a relatively high stress, or after the extrusion.

In some examples, the middle layer may be a relatively non-compliant layer that exhibits perforation or partial or complete rupture during inflation, so that the inner and outer layer may contact each other at one or more regions, or substantially contact across a major area of the inner layer, the outer layer, or the balloon following rupture or disintegration of the middle layer. A relatively compliant layer (also called a compliant layer herein) is a layer including a material that inflates, deflates or deforms without resulting in mechanical failure of the material. A relatively non-compliant layer (also called a non-compliant layer herein) is a layer including a material that resists inflation or deformation (relative to a compliant layer), for example, resulting in mechanical failure of the material in response to inflation or deformation beyond a predetermined threshold.

One or both of the delamination and the rupture of the middle layer may result in a multilayer balloon that includes inner and outer layers capable of independent movement, similar to the behavior of multilayer balloons formed by nesting structurally distinct balloons. However, one of the drawbacks to nesting multiple balloons may be that traditional nesting balloons require additional manufacturing steps such as aligning respective nested balloons to form the nested structure. The nesting step may also result in the introduction of air or fluid pockets between adjacent balloon surfaces, needing additional manufacturing steps for removal of fluid pockets to provide uniform inflation of the balloon. Example techniques and multilayer balloons according to the disclosure may provide a nested balloon configuration obtained from a single coextrusion, without requiring a nesting step for nesting separate balloons. Coextruding a single construction that results in a nested balloon configuration may thus be easier to manufacture compared to nesting individual balloons into a nested configuration. Thus, example techniques according to the disclosure may be used to prepare multilayer balloons including nested inner and outer layers.

Figure 1:
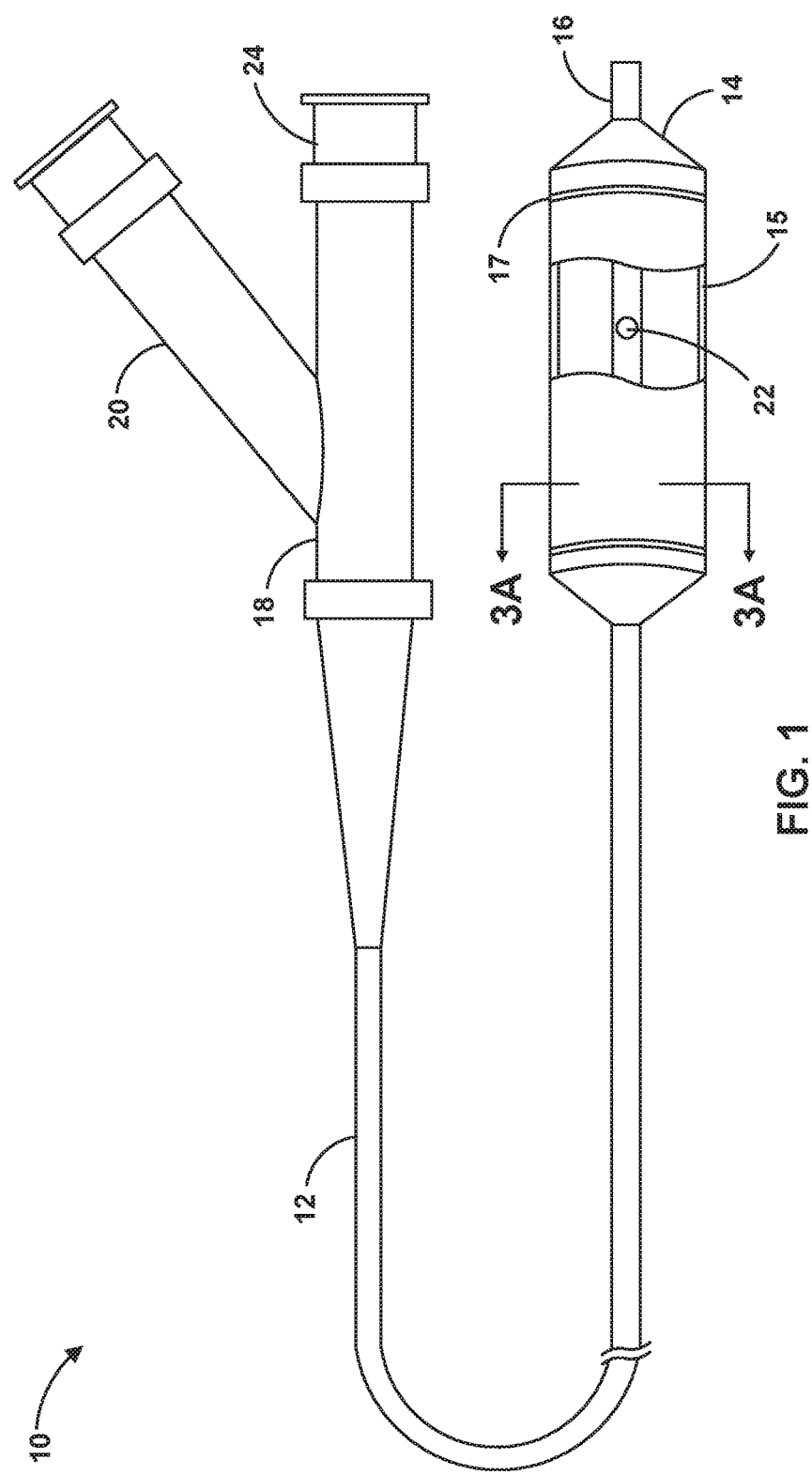
FIG. 1 is a schematic and conceptual side view of an example medical device including an elongated member and a balloon.

FIG. 1 is a schematic and conceptual side view of an example medical device 10 including an elongated member 12 and a balloon 14 mounted closer to a distal tip 16 of elongated member 12 than a proximal end of elongate member 12. A hub 18 connected to the proximal end of elongated member 12 may allow elongated member 12 to be manipulated, advanced, or retracted, and may provide ports for communicating with lumens defined by elongated member 12. For example, hub 18 may include an inflation arm 20 that may be connected to a source of inflating fluid to deliver inflating fluid through an inflation lumen port 22 to inflate balloon 14, or deflate balloon 14 by withdrawing the inflating fluid. In some examples, hub 18 may include an adapter 24 to receive a guidewire through a guidewire lumen in elongated member 12 (not shown). In some examples, elongated member 12 may include a catheter body, for example, a balloon catheter, and hub 18 may include a catheter hub. In some examples, instead of a guidewire catheter, medical device 10 may include a rapid-exchange balloon catheter system.

Elongated member 12 may be advanced to a target site, for example, through a body lumen such as a blood vessel of a patient. In some examples, distal tip 16 may be introduced into the vasculature of the patient through an incision or opening, followed by a shaft of elongated member 12. Elongated member 12 may be advanced through the body lumen, for example, over a guidewire introduced through adapter 24 of hub 18. Balloon 14 may be maintained in an uninflated or partly inflated configuration while advancing elongated member 12 through the vasculature. When elongated member 12 is sufficiently advanced, for example, such that balloon 14 is adjacent the target site, inflating fluid may be delivered through inflation lumen port 22 to inflate balloon 14 to an inflated configuration at the target site. Balloon 14 is illustrated in an inflated configuration in FIG. 1. In some examples, inflation of balloon 14 may result in expansion of the vasculature, or removal of blockage, for example, clots, debris, or fat at the target site. The inflating fluid may subsequently be withdrawn through inflation lumen port 22 to result in deflation of balloon 14, and deflated balloon 14 may be withdrawn through the vasculature by retracting elongated member 12.

In some examples, balloon 14 may include one or more radiopaque markers 17. For example, radiopaque marker 17 may include one or more radiopaque bands disposed about balloon 14, such as one marker 17 adjacent the proximal end of balloon 14 and another marker 17 adjacent a distal end of balloon 14, as shown in FIG. 1. Radiopaque marker 17 may allow balloon 14 to be observed using suitable radioimaging techniques during a medical procedure, for example, while advancing or retracting balloon 14 with elongated member 12.

Figure 2:
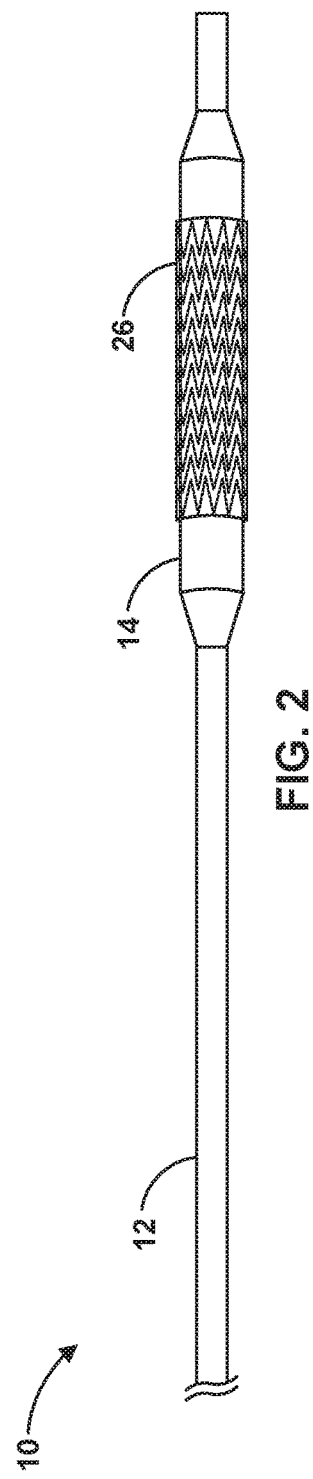
FIG. 2 is a schematic and conceptual partial side view of the example medical device of FIG. 1 further including a second medical device secured to the balloon.

In some examples, medical device 10 may include a second medical device 26. FIG. 2 is a schematic and conceptual partial side view of medical device 10 of FIG. 1 further including second medical device 26 positioned over (e.g., co-axial with) balloon 14, and, in some examples, secured to balloon 14. In some examples, as illustrated in FIG. 2, second medical device 26 may include a stent crimped to balloon 14. Balloon 14 is illustrated in an uninflated configuration in FIG. 2, with the stent in an unexpanded configuration ready for deployment. In examples in which second medical device 26 is secured to balloon 14, second medical device 26 may be advanced with balloon 14 to the target site, and the inflation of balloon 14 may trigger deployment of second medical device 26. For example, in examples in which second medical device 26 includes a stent, inflation of balloon 14 may expand the stent to an expanded state to scaffold a region of the vasculature adjacent the stent. In examples in which second medical device 26 was secured to balloon 14, after deploying second medical device 26 at a target site within the patient and subsequently partially or fully deflating balloon 14, second medical device 26 may remain in a deployed configuration at the target site, and only balloon 14 can be withdrawn from the patient. In other examples, second medical device 26 may be withdrawn with balloon 14 after balloon 14 is partly or completely deflated.

Balloon 14 may be defined by a balloon wall 15. Balloon wall 15 includes multiple layers, such that balloon 14 is a multilayer balloon. Balloon 14 and balloon wall 15 are further described with reference to FIGS. 3A-3D, which illustrate schematic and cross-sectional views of balloon 14 in different configurations, the cross-section being taken in a direction orthogonal to a longitudinal axis of elongated member 12 (FIG. 1). FIG. 3A is a schematic and conceptual cross-sectional view of balloon 14a, which is similar to balloon 14 of FIG. 1, in a partly inflated configuration. Balloon wall 15 includes outer layer 32 and inner layer 36. In some examples, outer layer 32 defines an outermost surface of balloon 14a, while inner layer 36 defines an innermost surface of balloon 14a. However, in some examples, balloon 14a may include one or more additional layers. In addition, in some examples, one or more coatings or surface treatments may be applied to outer layer 32, such as, but not limited to, a lubricious coating, a lubricious surface treatment or a therapeutic agent. Outer layer 32 and inner layer 36 may be formed of an inflatable material, for example, a polymer composition. In some examples, outer layer 32 and inner layer 36 may have the same composition. In some examples, outer layer 32 and inner layer 36 may have different compositions.

In some examples, balloon 14a includes at least one middle layer 34 disposed between outer layer 32 and inner layer 36, as shown in FIG. 3A. In some examples, middle layer 34 is formed of a material configured to have relatively poor adhesion to or relatively easy delamination from one or both of outer layer 32 and inner layer 36. In some examples, middle layer 34 may be coextensive with one or both of inner layer 36 and outer layer 32. In some examples, middle layer 34 may define at least one of a discontinuity, a perforation, a window, or another such opening, such that outer layer 32 and inner layer 36 may contact each other directly through the opening. In some examples, the discontinuity, the perforation, the window, or the opening may form in middle layer 34 as a result of expansion or inflation of middle layer 34. In some examples, middle layer 34 may define the discontinuity, the perforation, the window, or the opening before expansion or inflation. For example, middle layer 34 may be coextruded with one or both of inner layer 36 and outer layer 32 such that middle layer 34 defines the discontinuity, the perforation, the window, or the opening.

The layers of balloon 14a may be formed from any suitable materials that provide the properties described herein. In some examples, one or more of outer layer 32, middle layer 34, and inner layer 36 may include one or more of acrylonitrile-butadiene styrene (ABS), polyamides, for example, nylons, polyamide 6 (PA 6), or polyamide 66 (PA 66), polycarbonates (PC), polyethylenes (for example, high density polyethylenes (HDPE) or low density polyethylenes (LDPE)), poly(methyl methacrylate) (PMMA), polyoxymethylene (POM), polypropylenes (PP), polystyrenes (PS), polybutylene terephthalate (PBT), styrene acrylonitrile resin (SAN), thermoplastic elastomers (TPE) (for example, polyether block amides (PEBAs)), polyphenylene sulfide (PPS), polyetheretherketones (PEEK), polyurethanes, polyesters, or blends, copolymers, or coextrusions thereof. For example, one or more of outer layer 32, middle layer 34, and inner layer 36 may include sublayers, for example, coextruded layers. In some examples, the TPEs (or PEBAs) may include materials sold under the PEBAX® brand name (Arkema, Paris, France) or VESTAMID (Evonik Industries, Essen, Germany).

TABLE 1

| Material | ABS | PA 6 | PA 66 | PC | HDPE | LDPE | PMMA | POM | PP | PS | PBT | SAN | TPE | PPS |
|---|---|---|---|---|---|---|---|---|---|---|---|---|---|---|
| ABS |   |   |   |   | P | P |   |   | P | P |   |   |   |   |
| PA 6 |   |   |   |   | P | P |   |   | P |   |   |   |   |   |
| PA 66 |   |   |   | P | P | P |   |   | P |   |   |   |   |   |
| PC |   |   | P |   | P | P |   |   | P | P |   |   |   |   |
| HDPE | P | P | P | P |   |   | P | P | P | P | P | P | P |   |
| LDPE | P | P | P | P |   |   | P | P |   | P | P | P | P |   |
| PMMA |   |   |   |   | P | P |   |   | P |   |   |   |   |   |
| POM |   |   |   |   | P | P |   |   | P | P |   |   |   |   |
| PP | P | P | P | P | P |   | P | P |   | P | P | P |   |   |
| PS | P |   |   | P | P | P |   | P | P |   | P | P | P |   |
| PBT |   |   |   |   | P | P |   |   | P | P |   |   |   |   |
| SAN |   |   |   |   | P | P |   |   | P | P |   |   |   |   |
| TPE |   |   |   |   | P | P |   |   |   | P |   |   |   |   |
| PPS |   |   |   |   |   |   |   |   |   |   |   |   |   |   |

In some examples, middle layer 34 may include a material selected to have relatively poor adhesion to outer layer 32 and inner layer 36. Poor adhesion may be evaluated using a polymer welding compatibility matrix as a guide. In some examples, pairs of materials that form bad welding joints, fail to form a welding joint, or otherwise poorly adhere to each other may be potential pair materials ("P") as indicated by TABLE 1. One of a respective potential pair (for example, TPE and HDPE) may be selected for middle layer 34 and the other of the respective potential pair may be selected for one or both of outer layer 32 and inner layer 36. For example, both outer layer 32 and inner layer 36 may include a TPE such as a PEBA, for example, PEBAX® 7033 or 7233, and middle layer 34 may include a thermoplastic, for example, an HDPE, so that middle layer 34 has poor adhesion with outer layer 32 and inner layer 36.

While in the examples shown in FIGS. 3A-3D, balloons 14a, 14b, 14c, and 14d are illustrated having a circular cross-section, in some examples, balloons 14, 14b, 14c, and 14d may have any suitable shape, configuration, or cross-section. In some examples, balloon 14 may have a geometrically similar shape in an uninflated and an inflated configuration. For example, balloon 14 may be cylindrical in both uninflated and inflated configurations. In some examples, balloon 14 may have different shapes in uninflated and inflated configurations. For example, balloon 14 may be folded or otherwise have a compact uninflated configuration.

While in the examples shown in FIGS. 3A-3D, balloons 14a, 14b, 14c, and 14d are illustrated as having two or three layers, in some examples, balloons 14a, 14b, 14c, and 14d may have any number of additional layers, and the number of layers may change after one or more of delamination, perforation, rupture, or disintegration of balloon 14 or part of balloon 14. In some examples, one or more tie layers may be provided between adjacent layers of balloon 14. For example, a tie layer may include an adhesive to promote adhesion of adjacent layers. In some examples, one or more lubricant layers may be provided between adjacent layers of balloon 14. For example, the lubricant layer may include a lubricant to reduce adhesion between adjacent layers. In some examples, the lubricant may include one or more of silicone, graphene, or a graphitic coating. Providing a lubricant layer may promote delamination by reducing a joining compatibility between layers adjacent the lubricant layer.

In some examples, middle layer 34 may include a non-compliant layer. A non-compliant layer may be a layer that has lower flexibility, lower softness, higher rigidity, or compliance to expansion or inflation compared to a compliant layer. A compliant layer, for example, a layer including a PEBA, may exhibit stretching in response to an inflationary pressure. In contrast, a non-compliant layer, for example, a layer including an HDPE, may exhibit reduced or relatively no stretching compared to a compliant layer. Whether a layer is compliant or non-compliant may depend on the composition, hardness, and dimensions, for example, thickness, of the layer. Compliance may be measured, for example, by measuring radial expansion of a layer as a ratio of inflation pressure. In some examples, a compliant layer may exhibit an expansion greater than about 10 millimeters/atmospheres (mm/atm), or greater than about 20 millimeters/atmospheres, or greater than about 50 millimeters/atmospheres. In some examples, a non-compliant layer may exhibit an expansion lower than about 0.02 mm/atm, or lower than about 0.01 mm/atm, or lower than about 0.001 mm/atm. A semi-compliant layer may exhibit an expansion greater than about 0.02 mm/atm and less than about 10 mm/atm. In some examples, middle layer 34 may include a semi-compliant layer.

In some examples, outer layer 32 may have a thickness between about 0.005 millimeters (mm) and about 0.10 mm, for example, for coronary balloon applications. The total thickness of balloon 14 may be higher for non-coronary balloon applications, for example, up to 1 mm. In some examples, middle layer 34 may have a thickness between about 0.001 mm and about 0.10 mm. In some examples, inner layer 36 may have a thickness between about 0.005 and about 0.10 mm. In some examples, one or more of outer layer 32, middle layer 34, or outer layer 36 may have a hardness between about 25 Shore D and about 75 Shore D.

The hardness of respective layers of balloon 14 may vary. For example, the hardness of respective layers may increase from an outermost layer to an innermost layer of balloon 14. In some examples, the hardness of respective layers may decrease from an outermost layer to an innermost layer of balloon 14. For example, outer layer 32 may be softer than middle layer 34 to facilitate printing of patterns, instructions, or text, or to facilitate securing or crimping of second medical device 26 to balloon 14. In some examples, the hardness of a respective middle layer or layers may be higher than the hardness of respective inner and outer layer or layers. In some examples, an inner layer or layers may have substantially the same hardness as an outer layer or layers of balloon 14. In some examples, outer layer 32 and inner layer 36 may each be more flexible than middle layer 34. Thus, in examples in which middle layer 34 includes a non-compliant layer, the non-compliant layer may have a greater stiffness than each of inner layer 36 and outer layer 32. Middle layer 34 may be softer, more flexible, or both softer and more flexible than outer layer 32 and inner layer 36 to provide a predetermined softness to balloon 14.

In some examples, a compliance of a layer of balloon 14 may be reduced by adding components, for example, reinforcing material or fibers that resist stretching or inflation. For example, one or more of outer layer 32, middle layer 34, and inner layer 36 may include one or more reinforcing components, materials, or fibers. In some examples, the reinforcing components may include one or more of glass, metal, alloy, carbon, or polymers.

In some examples, middle layer 34 may be configured to delaminate from outer layer 32 and inner layer 36 in an inflated configuration of balloon 14a, for example, a fully inflated configuration of balloon 14a. In some examples, middle layer 34 may delaminate from outer layer 32 and inner layer 36 when balloon 14a is inflated to a predetermined delamination pressure. For example, middle layer 34 may have relatively low welding or joining compatibility with one or both of outer layer 32 and inner layer 36 such that middle layer 34 may separate from one or both of outer layer 32 and inner layer 36 as balloon 14a is inflated to the predetermined pressure to result in delamination. In some examples, the predetermined pressure may be between about 0.1 atmospheres (atm) and 45 atm. While inflating may result in delamination, in some examples, middle layer 34 may separate from one or both of outer layer 32 and inner layer 36 in an uninflated configuration of balloon 14a (for example, without inflation or prior to inflation) to result in delamination. FIG. 3B is a schematic and conceptual expanded view of the cross-sectional view of an example balloon 14b similar to balloon 14a shown in FIG. 3A in an inflated delaminated configuration. In the delaminated configuration illustrated in FIG. 3B, a balloon wall 15b of balloon 14b includes middle layer 34 delaminated from outer layer 32 and inner layer 36. For example, delamination may be a state in which an inner surface 32b of outer layer 32 is separated from an outer surface 34a of middle layer 34, and an outer surface 36a of inner layer 36 is separated from an inner surface 34b of middle layer 34.

In some examples, inner surface 32b of outer layer 32 and outer surface 34a of middle layer 34 may define a first inter-layer void 35a, and outer surface 36a of inner layer 36 and inner surface 34b of middle layer 34 may define a second inter-layer void 35b. One or both of first and second inter-layer voids 35a or 35b may exhibit a vacuum or a pressure lower than a pressure within an interior volume defined by inner layer 36. In some examples, rupture or perforation of middle layer 34 may cause first and second inter-layer voids 35a or 35b to be fluidically connected. In some examples, debris or material originating from rupture or perforation of middle layer 34 may occupy one or both of first and second inter-layer voids 35a or 35b.

While the layers are illustrated as being physically separated with intermediate spacing in the example illustrated in FIG. 3B, in some examples, the layers may be substantially in contact (e.g., in contact along only some parts of the layers or along the entire adjacent surfaces) in the delaminated configuration. For example, the delamination may entail loss of adhesion between respective surfaces of respective layers, while still maintaining or being succeeded by contact between the respective surfaces of respective layers. In some examples, delamination of middle layer 34 from outer layer 32 and inner layer 36 may result from relatively poor weld, adhesion, or joining compatibility between pairs of respective materials of outer layer 32 and middle layer 34, and inner layer 36 and middle layer 34, as indicated by poor compatibility of potential pair materials in TABLE 1.

Outer layer 32, middle layer 34, and inner layer 36 may be capable of independent movement, for example, expansion or contraction, in the delaminated configuration. For example, one or both of outer layer 32 or inner layer 36 may be capable of independent movement relative to middle layer 34, or one or both of middle layer 34 or inner layer 36 may be capable of independent movement relative to outer layer 32, or even one or both of middle layer 34 or outer layer 32 may be capable of independent movement relative to inner layer 36. Thus, in some examples of the delaminated configuration illustrated in FIG. 3B, balloon 14b may behave similar to a nested series of balloons formed from a first balloon including outer layer 32, a second balloon including middle layer 34, and a third balloon including inner layer 36. For example, the first, second, and third balloons may be fluidically isolated from each other. A balloon wall of a predetermined thickness including fluidically isolated nested balloons may exhibit better puncture resistance and robustness compared to a balloon wall including a single layer or a laminated multilayer having the same thickness. For example, a puncture in an outer surface of a single layer or laminated multilayer balloon may propagate to an inner surface across the balloon wall, leading to balloon failure. In contrast, a puncture in an outermost balloon of a series of fluidically isolated nested balloons may not propagate to an innermost balloon, such that even if an outermost balloon is punctured, at least one unpunctured innermost layer will remain inflated.

In some examples, middle layer 34 includes the non-compliant layer. Balloon 14a may thus include non-compliant middle layer 34 coextruded on inner layer 36, and outer layer 32 coextruded on middle layer 34. Non-compliant middle layer 34 may be configured to delaminate from outer layer 32 and inner layer 36 in an inflated configuration of balloon 14a. In some examples, non-compliant middle layer 34 may be configured to delaminate from inner layer 36 before delaminating from outer layer 32. For example, the joining compatibility of the pair of materials of non-compliant middle layer 34 and of inner layer 36 may be lower than the joining compatibility of the pair of materials of non-compliant middle layer 34 and outer layer 32. In other examples, non-compliant middle layer 34 may be configured to delaminate from outer layer 32 before delaminating from inner layer 36. For example, the joining compatibility of the pair of materials of non-compliant middle layer 34 and of outer layer 32 may be lower than the joining compatibility of the pair of materials of non-compliant middle layer 34 and inner layer 36. Thus, middle layer 34 may promote delamination of one or more layers of balloon 14. In some examples, balloon 14 may include additional layers that promote delamination. For example, balloon 14 may include more than one layer that promotes delamination, for example, non-compliant layers or lubricant layers, to further improve delamination of predetermined layers of balloon 14.

In examples in which middle layer 34 includes a non-compliant layer, inflating balloon 14a beyond a predetermined pressure may cause middle layer 34 to perforate, or partly or completely rupture, while outer layer 32 and inner layer 36 remain intact and act to maintain balloon 14a in an inflated or inflatable state. For example, FIG. 3C is a schematic and conceptual cross-sectional view of an example balloon 14c similar to balloon 14a of FIG. 3A including middle layer 34 in an inflated perforated configuration. In some examples, a balloon wall 15c of balloon 14c includes middle layer 34 defining a plurality of perforations 34c. In some examples, when balloon 14a of FIG. 3A is inflated to a predetermined pressure, middle layer 34 at least partly ruptures or perforates, forming balloon 14c shown in FIG. 3C. While inner surface 32b of outer layer 32 is shown spaced from outer surface 36a of inner layer 36, in some examples, inner surface 32b of outer layer 32 may contact outer surface 36a of inner layer 36 at least at regions defined by perforations 34c, i.e., outer layer 32 and inner layer 36 may contact each other through the open spaces defined by perforations 34c, for example, through first or second inter-layer voids 35a or 35b. In some examples, as shown in FIGS. 3B and 3C, first and second inter-layer voids 35a and 35b of balloon 14b may combine to form a combined inter-layer void 35 of balloon 14c after rupture or perforation of middle layer 34, and perforations 34c may extend through combined inter-layer void 35.

In examples in which middle layer 34 includes a non-compliant layer, the non-compliant layer is configured to rupture in the inflated configuration at a predetermined pressure. The predetermined pressure is insufficient to rupture both inner layer 36 and outer layer 32, thereby maintaining balloon 14a in an inflated or inflatable state. In some examples, the non-compliant layer may be configured to rupture after delamination of the non-compliant layer from inner layer 36 and outer layer 32. In some examples, the non-compliant layer may be configured to fragment in the inflated configuration at the predetermined pressure.

In some examples, inflating balloon 14a to the predetermined pressure sufficient to cause one or both of delamination and rupture may be performed as part of a technique for manufacturing balloon 14a, as described with reference to some example techniques according to the disclosure, for example, techniques described with reference to FIGS. 4 and 5. In addition to, or instead of delaminating during the manufacturing stage, in some examples, inflating balloon 14a to the predetermined pressure sufficient to cause one or both of delamination and rupture may be performed by a medical practitioner while using medical device 10, as described with reference to some example techniques according to the disclosure, for example, techniques described with reference to FIGS. 4 and 5. In some examples, after inflating balloon 14a to the predetermined pressure, balloon 14a may be deflated to allow folding or otherwise compacting balloon 14a to facilitate packaging and use.

In some examples, the perforations, rupture, or tears in middle layer 34 may cause middle layer 34 to substantially disintegrate in an inflated configuration of balloon 14a, so that middle layer 34 no longer separates outer layer 32 and inner layer 36. For example, FIG. 3D is a schematic and conceptual cross-sectional view of an example balloon 14d similar to balloon 14a of FIG. 3A with inner layer 36 directly contacting outer layer 32. For example, a balloon wall 15d of balloon 14d may include inner surface 32b defined by outer layer 32 substantially uniformly (e.g., uniformly or nearly uniformly) contacting outer surface 36a defined by inner layer 36 in the inflated configuration of balloon 14d. Outer layer 32 and inner layer 36 may be capable of independent movement, for example, expansion or contraction, in the inflated configuration shown in FIG. 3D. Thus, in the inflated configuration illustrated in FIG. 3D, balloon 14d may behave similar to a nested pair of balloons formed from a first balloon including outer layer 32, and a second balloon including inner layer 36. For example, inner layer 36 may define an inner balloon, and outer layer 32 may define an outer balloon, with the inner balloon being nested in the outer balloon. In some examples, the inner balloon may be fluidically isolated from the outer balloon. For example, a loss of pressure or increase in pressure in one of the inner or the outer balloons may not affect the pressure in the other of the inner or the outer balloons. If second medical device 26, for example, a stent, punctures the outer balloon, at least an inner balloon may still remain pressurized, maintaining balloon 14d inflated. Similarly, if the outer balloon punctures as a result of contact with a calcified lesion or another rigid structure within a body lumen, at least an inner balloon may still remain pressurized, maintaining balloon 14d inflated.

Each of the delaminated configuration of balloon 14d shown in FIG. 3D and the inflated configurations of balloons 14c and 14d respectively shown in FIGS. 3C and 3D may exhibit higher burst or puncture resistance compared to a single layer balloon having the same respective effective wall thickness as respective balloon walls 15b, 15c, and 15d. For example, a puncture in an outer surface of a single layer or laminated multilayer balloon may propagate to an inner surface across the balloon wall, leading to balloon failure. In contrast, the first, second, and third layers may form nested balloons that are fluidically isolated from each other, preventing a loss of pressure in an outermost balloon from resulting in a loss of pressure in an innermost balloon. A puncture in an outermost balloon of a series of fluidically isolated nested balloons may not propagate to an innermost balloon, such that even if an outermost balloon is punctured, at least one unpunctured innermost layer will remain inflated, maintaining the structural integrity and function of the balloon. Thus, example multilayer balloons according to the disclosure may be used in procedures where robustness and puncture-resistance of balloons is desired.

Figure 4:
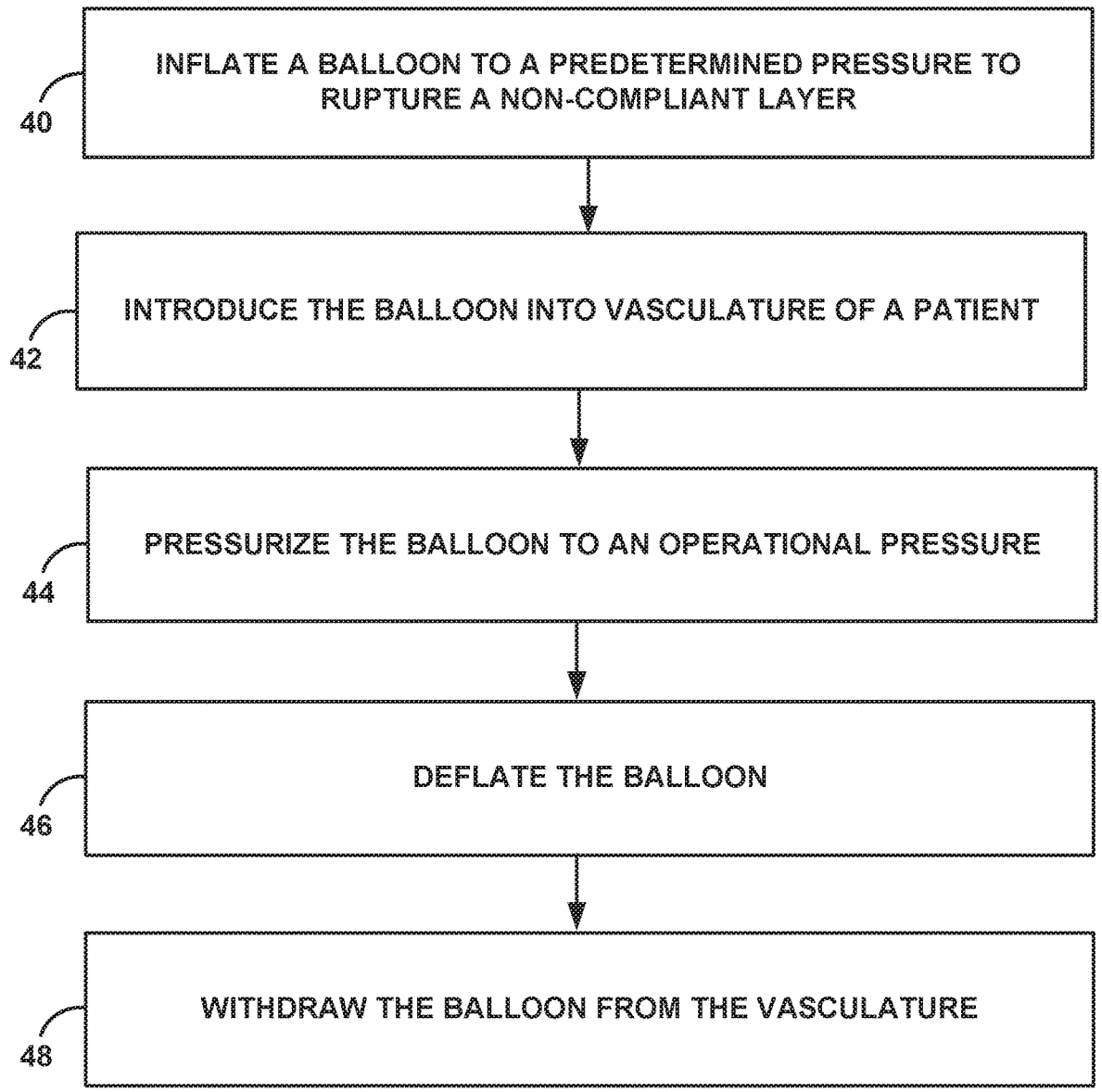
FIG. 4 is a flowchart illustrating an example technique for using an example balloon in a procedure.

FIG. 4 is a flowchart illustrating an example technique for using balloon 14 in a procedure. As discussed with reference to FIGS. 3A-3D, in some examples, balloons 14a-14d may include middle layer 34 including a non-compliant layer coextruded on inner layer 36, and outer layer 32 coextruded on the non-compliant layer. While the example technique of FIG. 4 is described with reference to balloon 14 shown in FIG. 1, balloons 14a-14d shown in FIGS. 3A-3D may be representative of different configurations of balloon 14 of FIG. 1, for example, during performing the example technique of FIG. 4. The example technique of FIG. 4 optionally includes inflating balloon 14 to the predetermined pressure sufficient to rupture the non-compliant layer, and insufficient to rupture both inner layer 36 and outer layer 32 (40). As discussed below, inflating balloon 14 to the predetermined pressure (40) may not be required if inflating balloon 14 to an operational pressure would result in rupture of the non-compliant layer or middle layer 34 without rupturing both inner layer 36 and outer layer 32. For example, the operational pressure may be greater than or equal to the predetermined pressure, and inflating to the operational pressure may therefore result in rupture of the non-compliant layer, without requiring a separate inflating of balloon 14 to the predetermined pressure.

Inflating balloon 14 may include delivering inflating fluid to balloon 14 through inflation lumen port 22 causing balloon 14 to expand to an inflated ruptured configuration, for example, the configuration of balloon 14c shown in FIG. 3C, in which middle layer 34 is at least partly perforated or ruptured, or the configuration of balloon 14d shown in FIG. 3D, in which middle layer 34 is substantially ruptured or disintegrated. In some examples, inflating balloon 14 to the predetermined pressure (40) may result in delamination of one or both of outer layer 32 from middle layer 34 or of middle layer 34 from inner layer 36. For example, outer layer 32 may delaminate from middle layer 34, or middle layer 34 may delaminate from inner layer 36, during the inflating, as shown in FIG. 3B (40). In some examples, at least partial delamination may occur before the rupture of middle layer 34. For example, at least a portion of one of outer layer 32, middle layer 34, and inner layer 36 may separate from a portion of another of outer layer 32, middle layer 34, and inner layer 36, before the rupture of any portion of middle layer 34. In some examples, complete delamination may occur before the rupture of middle layer 34. For example, outer layer 32 may completely delaminate from middle layer 34, and middle layer 34 may completely delaminate from inner layer 36, before the rupture of any portion of middle layer 34. In other examples, delamination may be at least partly concurrent in time with rupture during the inflating (40). For example, at least a portion of one of outer layer 32, middle layer 34, and inner layer 36 may separate from a portion of another of outer layer 32, middle layer 34, and inner layer 36 during rupture of a portion of middle layer 34.

In some examples, inflating balloon 14 to the predetermined pressure (40) may be performed before initiating a medical procedure, for example, after removing balloon 14 from a medical package, or while balloon 14 is in the medical package. In addition, or instead, inflating balloon 14 to the predetermined pressure (40) may be performed during manufacture of balloon 14, for example, during or after coextruding outer layer 32, middle layer 34, and inner layer 36 so that balloon 14 is in a configuration similar to that of balloon 14c or balloon 14d in the medical package.

In some examples, the technique of FIG. 4 includes introducing balloon 14 into vasculature of a patient (42). For example, distal tip 16 of elongated member 12 may be introduced at an incision or body opening and into the vasculature, followed by the shaft of elongated member 12 carrying balloon 14. In some examples, introducing balloon 14 into the vasculature (42) may include advancing balloon 14 carried on elongated member 12 over a guidewire or other guide member through the vasculature to a target site within the vasculature. In examples in which balloon 14 includes radiopaque marker 17, a clinician may use radiopaque marker 17 to visualize the position of balloon 14a relative to the target site within the vasculature, for example, by radioimaging. In another example, inflating balloon 14 to the predetermined pressure (40) may be performed after introducing balloon 14 into the vasculature (42).

After balloon 14 arrives at the target site, balloon 14 may be inflated, such as by pressurizing the balloon to an operational pressure (44). The operational pressure may be a pressure sufficient to expand balloon 14 to an operational dimension, for example, an operational diameter. For example, the operational diameter may be an average diameter of balloon 14 in an inflated configuration that is sufficient to expand, clear, or scaffold a region of the vasculature adjacent the target site. In some examples, the operational diameter may be a diameter sufficient to deploy second medical device 26 at the target size, for example, by causing second medical device 26 to expand, move, or decouple from balloon 14 or elongated member 12, and occupy the target site. In some examples, the operational pressure may be more, less, or the same as the predetermined pressure. In another example, balloon 14 may not be inflated to the predetermined pressure (40) prior to introducing balloon 14 into vasculature of a patient (42). Rather, pressurizing the balloon to an operational pressure (44) may sufficiently rupture the non-compliant layer of middle layer 34.

In some examples, the technique of FIG. 4 includes, after the pressurizing (44), deflating balloon 14 (46). A clinician may, for example, withdraw inflating fluid from inflating lumen port 22 to cause balloon 14 to depressurize and contract, shrink, collapse, fold, or otherwise attain a compact configuration allowing safe withdrawal of balloon 14a from the vasculature. After deflating balloon 14 (46), the clinician may withdraw balloon 14 from the vasculature (48). For example, elongated member 12 carrying balloon 14 may be withdrawn from the vasculature.

While the example technique of FIG. 4 is described with respect to the vasculature, the example technique of FIG. 4 may be used to advance and deploy balloon 14 at a target site within any body lumen accessible through a body opening or incision. Thus, an example technique for using balloon 14 has been described with reference to FIG. 4.

Example techniques for manufacturing or preparing balloon 14 are described with reference to FIG. 5, which is a flowchart illustrating an example technique for manufacturing balloon 14. In some examples, the technique of FIG. 5 may include coextruding a non-compliant layer on inner layer 36 (50), and coextruding outer layer 36 on the non-compliant layer (52). As described with reference to FIGS. 3A-3D, in some examples, middle layer 34 includes the non-compliant layer. In some examples, inner layer 36, middle layer 34 including the non-compliant layer, and outer layer 32 are coextruded simultaneously. For example, respective heated, flowable, or molten compositions for inner layer 36, middle layer 34, and outer layer 32 may be coextruded from an extrusion die onto a substrate, for example, a mandrel. As described elsewhere in the disclosure, coextrusion of the different layers may be used to obtain a nested configuration of balloons without requiring a nesting step. A nesting step including nesting individual balloons may introduce fluid or air pockets or other non-uniformities in the balloon structure. In contrast, coextrusion of multiple layers results in a uniform balloon structure. In some examples, the technique of FIG. 5 may include coextruding a tubing including inner layer 36, middle layer 34 including the non-compliant layer, and outer layer 32.

In other examples, inner layer 36, middle layer 34, and outer layer 32 may be coextruded as a multilayer sheet, for example, by coextruding onto a flat substrate. In some examples, inner layer 36, middle layer 34 including the non-compliant layer, and outer layer 32 may be sequentially extruded. In some examples, a pair of layers may be coextruded, followed by extrusion of another layer. For example, middle layer 34 and inner layer 36 may be coextruded, followed by extrusion of outer layer 32 on the coextruded structure. In some examples, middle layer 34 and outer layer 32 may be coextruded, followed by extrusion of inner layer 36 on the coextruded structure. In some examples, the order of layers during extrusion or coextrusion may be different from the order of layers in balloon 14. For example, when balloon 14 includes three or more layers, pairs or groups of layers may be coextruded, and reordered, stacked or otherwise combined in a mold followed by pressurizing in the mold to eventually form balloon 14.

In some examples, the extrusion or coextrusion die for middle layer 34 may be configured to extrude middle layer 34 defining at least one of a discontinuity, a perforation, a window, or an opening. In some examples, the discontinuity, the perforation, the window, or the opening may be stamped, cut, or otherwise formed in middle layer 34 after extrusion or coextrusion of middle layer 34, and before middle layer 34 is eventually assembled into the multilayer wall 15a of balloon 14a.

Balloon 14 may be formed from the multilayer tube or sheet including inner layer 36, middle layer 34 including the non-compliant layer, and outer layer 32 (54). For example, the multilayer tube or sheet may be placed in a mold configured to provide the shape of the balloon, and may be expanded to occupy the periphery of the mold before the tube or sheet has cooled or otherwise cured or solidified. In some examples, the respective compositions for inner layer 36, middle layer 34 including the non-compliant layer, and outer layer 32 may be directly coextruded into the mold, so that balloon 14 is shaped during coextrusion. In some examples, one or more of inner layer 36, middle layer 34, and outer layer 32 may be extruded onto a reinforcing substrate, for example, a reinforcing fabric, an or an arrangement of reinforcing components or fibers. In some examples, reinforcing components may be introducing during the coextrusion.

The coextruding (50 and 52) may include stretching balloon 14. For example, a region or side of balloon 14 may be intermittently heated or stretched during or after the coextruding. In some examples, the stretching may include double stretching, or stretching balloon 14 from two sides. In some examples, the stretching may include a primary stretching at a first pressure followed by a secondary stretching at a second pressure. The stretching may promote a uniform wall thickness and promote uniform inflation of balloon 14.

Figure 5:
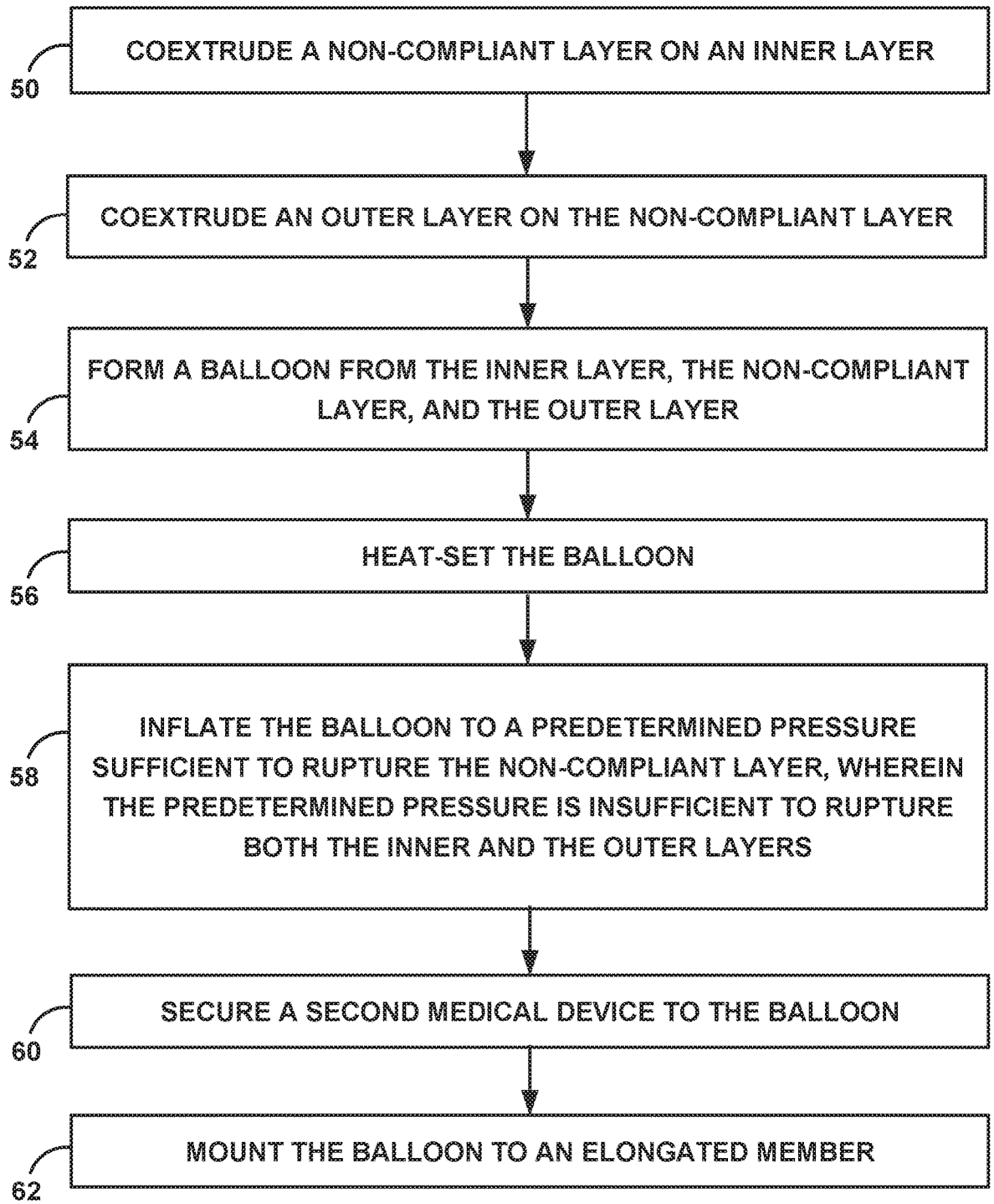
FIG. 5 is a flowchart illustrating an example technique for preparing an example balloon.

In some examples, the technique of FIG. 5 includes heat-setting balloon 14 (56). In some examples, heat-setting may include annealing, for example, heating and maintaining balloon 14 at a predetermined temperature for a predetermined period of time. The predetermined temperature may be near or above a melt transition of one or more of layers 32, 34, or 36, or near or above a glass transition temperature of one or more polymers in layers 32, 34, or 36. Heat-setting may remove creases, wrinkles, or marks from surfaces of balloon 14, and may further provide a uniform thickness to a wall of balloon 14, for example, wall 15a of balloon 14a. For example, heat-setting may also be used to control the wall thickness of wall 15a of balloon 14a. Heat-setting may be performed using any suitable technique. For example, balloon 14 may be heated in the mold, such that the heat-setting may provide a permanent set or shape for balloon 14. Heat-setting may be used to control compliance of one or more of layers 32, 34, or 36, or overall compliance and burst resistance of balloon 14. In some examples, the configuration of balloon 14 as molded and heat-set may correspond to an uninflated configuration of balloon 14. In some examples, the configuration of balloon 14 as molded and heat-set may correspond to an inflated configuration of balloon 14.

In some examples, the technique of FIG. 5 may include inflating balloon 14 to a predetermined pressure sufficient to rupture middle layer 34 including the non-compliant layer (58). The predetermined pressure is insufficient to rupture both inner layer 36 and outer layer 32. For example, inflating balloon 14 to the predetermined pressure may result in formation of structures corresponding to balloons 14a, 14, 14c, or 14d as described with reference to FIGS. 3A-3D. In some examples, the technique of FIG. 5 may include inflating balloon 14 to allow only the non-compliant layer to fragment at the predetermined pressure to cause inner surface 32b defined by outer layer 32 to contact outer surface 36a defined by inner layer 36.

In some examples, inflating balloon 14 to the predetermined pressure (58) may result in delamination of one or both of outer layer 32 from middle layer 34 or of middle layer 34 from inner layer 36. For example, outer layer 32 may delaminate from middle layer 34, or middle layer 34 may delaminate from inner layer 36, during the inflating (58). In some examples, at least partial delamination may occur before the rupture of middle layer 34. For example, at least a portion of one of outer layer 32, middle layer 34, and inner layer 36 may separate from a portion of another of outer layer 32, middle layer 34, and inner layer 36, before the rupture of any portion of middle layer 34. In some examples, complete delamination may occur before the rupture of middle layer 34. For example, outer layer 32 may completely delaminate from middle layer 34, and middle layer 34 may completely delaminate from inner layer 36, before the rupture of any portion of middle layer 34. In other examples, delamination may overlap with rupture during the inflating (58). For example, at least a portion of one of outer layer 32, middle layer 34, and inner layer 36 may separate from a portion of another of outer layer 32, middle layer 34, and inner layer 36 during rupture of a portion of middle layer 32.

While forming balloon 14 (54) may precede inflating balloon 14 (58) as shown in the example of FIG. 5. In other examples, balloon 14 may be inflated to the predetermined pressure sufficient to rupture non-compliant middle layer 34 during forming balloon 14 (54). Thus, one or both of delamination or rupture of non-compliant middle layer 34 may occur during forming balloon 14 (54), and the example technique may not include an additional or separate inflation of balloon 14 to the predetermined pressure sufficient to rupture balloon 14 (58).

In some examples, the technique of FIG. 5 may further include securing second medical device 26 to balloon 14 (60). For example, when second medical device 26 includes a stent, securing second medical device 26 to the balloon (60) may include crimping the stent to balloon 14.

In some examples, the technique of FIG. 5 may further include mounting balloon 14 to elongated member 12 (62). For example, elongated member 12 may include a catheter body, and balloon 14 may be mounted to the catheter body.

Other techniques for forming balloon 14 may be used in other examples.

Various examples have been described. These and other examples are within the scope of the following claims.

What is claimed is:

1. A method comprising:
    inflating a balloon to a predetermined pressure, wherein the balloon comprises a non-compliant layer coextruded on an inner layer and an outer layer coextruded on the non-compliant layer, wherein the predetermined pressure is sufficient to rupture the non-compliant layer and insufficient to rupture both the inner layer and the outer layer;
    deflating the balloon; and
    introducing the balloon into vasculature of a patient.

2. The method of claim 1, wherein inflating the balloon at the predetermined pressure comprises causing the non-compliant layer to rupture but not rupture the inner layer and the outer layer to cause an inner surface defined by the outer layer to contact an outer surface defined by the inner layer.

3. The method of claim 1, wherein inflating the balloon at the predetermined pressure comprises causing the non-compliant layer to rupture but not rupture the inner layer and the outer layer to cause the non-compliant layer to define at least one of a discontinuity, a perforation, a window, or an opening in the inflated configuration.

4. The method of claim 1, wherein inflating the balloon at the predetermined pressure comprises causing the non-compliant layer to delaminate from the inner and the outer layers and then rupture.

5. The method of claim 1, wherein the non-compliant layer has a greater stiffness than each of the inner layer and the outer layer.

6. The method of claim 1, wherein the inner layer and the outer layer are more flexible than the non-compliant layer.

7. The method of claim 1, wherein, when the balloon is introduced into the vasculature, the inner layer defines an inner balloon and the outer layer defines an outer balloon, the inner balloon being nested in the outer balloon.

8. The method of claim 7, wherein, when the balloon is introduced into the vasculature, the inner balloon is fluidically isolated from the outer balloon.

9. The method of claim 1, wherein the non-compliant layer comprises a thermoplastic, and wherein one or both of the inner layer and the outer layer comprises a thermoplastic elastomer.

10. The method of claim 1, wherein the non-compliant layer comprises a high-density polyethylene (HDPE), and wherein one or both of the inner layer and the outer layer comprises a polyether block amide (PEBA).

11. A method comprising:
    inflating a balloon to a predetermined pressure, wherein the balloon comprises a non-compliant layer coextruded on an inner layer and an outer layer coextruded on the non-compliant layer, wherein the predetermined pressure is sufficient to delaminate the non-compliant layer from the inner layer and the outer layer;
    deflating the balloon; and
    introducing the balloon into vasculature of a patient.

12. The method of claim 11, wherein inflating the balloon at the predetermined pressure comprises causing the non-compliant layer to delaminate from the inner layer and the outer layer but not rupture the inner layer and the outer layer.

13. The method of claim 11, wherein inflating the balloon at the predetermined pressure comprises causing the non-compliant layer to delaminate from the inner layer before delaminating from the outer layer.

14. The method of claim 11, wherein inflating the balloon at the predetermined pressure comprises causing the non-compliant layer to delaminate from the outer layer before delaminating from the inner layer.

15. The method of claim 11, wherein inflating the balloon at the predetermined pressure comprises causing the non-compliant layer to delaminate from the inner layer and the outer layer and rupture the non-compliant layer following the delamination.

16. The method of claim 11, wherein inflating the balloon at the predetermined pressure comprises causing the non-compliant layer to rupture but not rupture the inner layer and the outer layer to cause the non-compliant layer to define at least one of a discontinuity, a perforation, a window, or an opening in the inflated configuration.

17. The method of claim 11, wherein, when the balloon is introduced into the vasculature, the inner layer defines an inner balloon and the outer layer defines an outer balloon, the inner balloon being nested in the outer balloon.

18. The method of claim 17, wherein, when the balloon is introduced into the vasculature, the inner balloon is fluidically isolated from the outer balloon.

19. The method of claim 11, wherein the non-compliant layer comprises a thermoplastic, and wherein one or both of the inner layer and the outer layer comprises a thermoplastic elastomer.

20. The method of claim 11, wherein the non-compliant layer comprises a high-density polyethylene (HDPE), and wherein one or both of the inner layer and the outer layer comprises a polyether block amide (PEBA).

\* \* \* \* \*